(12) United States Patent
Sasso

(10) Patent No.: US 6,500,155 B2
(45) Date of Patent: Dec. 31, 2002

(54) SAFETY ANGLED INDWELLING NEEDLE AND A PROTECTIVE SHIELD FOR A SAFETY ANGLED INDWELLING NEEDLE

(75) Inventor: John T. Sasso, Gwynedd Valley, PA (US)

(73) Assignee: Churchill Medical Systems, Inc., Horsham, PA (US)

( * ) Notice: Subject to any disclaimer, the term of this patent is extended or adjusted under 35 U.S.C. 154(b) by 0 days.

(21) Appl. No.: 09/782,335

(22) Filed: Feb. 13, 2001

(65) Prior Publication Data

US 2002/0111581 A1 Aug. 15, 2002

(51) Int. Cl.[7] .............................................. A61M 25/00
(52) U.S. Cl. ........................ 604/177; 604/192; 604/263
(58) Field of Search ................................. 604/162, 192, 604/177, 263

(56) References Cited

U.S. PATENT DOCUMENTS

| | | | |
|---|---|---|---|
| 2,748,769 A | 6/1956 | Huber | |
| 4,627,843 A | * 12/1986 | Raines | ........................ 604/263 |
| 5,505,711 A | 4/1996 | Arakawa et al. | |
| 5,879,330 A | 3/1999 | Bell | |
| 5,921,969 A | 7/1999 | Vallelunga et al. | |
| 5,951,522 A | 9/1999 | Rosato et al. | |

* cited by examiner

*Primary Examiner*—Philippe Derakshani
(74) *Attorney, Agent, or Firm*—Caesar, Rivise, Bernstein, Cohen & Pokotilow, Ltd.

(57) ABSTRACT

A safety needle device including a right angled Huber needle and a protective shield. The protective shield includes a central hub having a passageway and a pair of wing members. The distal end of the needle projects out of the passageway perpendicular to the hub. Each of the wing members is a generally planar member mounted to the central hub so that each can be flexed from an open state, wherein they are generally coplanar with each other, to a closed state, wherein they abut each other with the distal portion of the needle disposed between them to enclose it. The wing members also include plural connectors for cooperation with each other to hold the wing members in the closed state.

23 Claims, 2 Drawing Sheets

SAFETY ANGLED INDWELLING NEEDLE AND A PROTECTIVE SHIELD FOR A SAFETY ANGLED INDWELLING NEEDLE

BACKGROUND OF THE INVENTION

This invention relates generally to hypodermic needles, and more particularly to safety indwelling angled needles, e.g., right angle Huber needles, and protective shields for such needles, to prevent accidental sticking when inserting or removing angled needles from the body of a living being.

As is known implanted ports for the delivery of drugs or other liquid materials are commonly utilized in the medical field today. Such ports are typically placed in a subcutaneous pocket, e.g., the anterior upper chest wall below the clavicle, and typically include a chamber for the drug or other liquid and a pierceable, e.g., rubber, septum for receipt of a needle to either fill or empty the chamber. Special non-coring needles (sometimes referred to as "Huber" needles) are commonly used with such ports to minimize the damage to the septum resulting from repeated piercing by the needle. Such damage may lead to infusion of the septum fragment(s) into the patient's vascular system or into any catheter or other device having access to the port, thereby occluding the port. In U.S. Pat. No. 2,748,759 (Huber) there is shown a Huber type safety needle.

As is known, Huber needles may be straight or angled and may be of various lengths depending upon the application, e.g., drawing blood, filling the chamber, flushing chamber, etc. In order to hold the needle in place in the port Huber needles frequently include a pair of flanges which are arranged to be secured, e.g., taped, to the patient's skin at the location of the port.

As will be recognized by those skilled in the art removal of a Huber needle from a port, particularly, a right angle shaped Huber needle, frequently results in an accidental piercing or "needle-stick" of the person removing the needle.

U.S. Pat. No. 5,505,711 (Arakawa et al.) discloses an indwelling injector needle device constructed to reduce the risk of accidental needle-sticks. The device includes a pair of wings and a cannula or needle body, a hub supporting a proximal end of the needle body, a tube in fluid communication with the needle body, a cylindrical holder having a distal end from which the wings protrude, and a latching mechanism. The hub can slide along an inner periphery of the holder between a first position near the distal end of the holder and a second position near a proximal end of the holder. A latching mechanism is formed in and disposed between the hub and the holder so that the hub is inhibited from moving from the first position toward the second position, and vice versa. The needle edge can be retracted within the holder while its wings remain fixed to a patient's skin.

U.S. Pat. No. 5,879,330 (Bell) discloses a needle retraction device for removing a needle, such as a right angled "Huber" needle, from a patient without danger of an accidental needle-stick. The device basically comprises an exterior housing having an interior compartment and a slidable member. The housing has an exterior wall which defines an interior compartment. The slidable member has a pair of spaced apart movable legs separated from one another by an elongate slot and is located within the interior compartment. The pair of spaced apart movable legs are also spaced from a remainder of the slidable member by a cavity or area which is sized to receive the needle. The slidable member is movable from a first position, in which the pair of spaced apart movable legs are located outside of the interior compartment of the needle retraction device for receiving a needle, and a second retracted position, in which the pair of spaced apart movable legs along with a supported needle, are completely retracted inside the interior compartment of the housing to prevent an inadvertent needle stick.

U.S. Pat. No. 5,921,969 (Vallenunga et al.) discloses a device for shielding a butterfly needle, such as a straight or right angled "Huber" needle, to protect the user against accidental needle-stick injuries. The device basically comprises a hollow box-like member having a pair of engaging complementary shield sections which are adapted to be secured together to form a cavity for receipt of the needle therein.

U.S. Pat. No. 5,951,522 (Rosato et al.) also discloses a device whose intent is to reduce accidental needle-sticks caused by right angled Huber type needles. To that end the device of this patent is in the form of hypodermic needle safety enclosure for a right angle shaped hypodermic needle. A wing assembly is mounted on the hypodermic needle. The wing assembly may be either a single integral member having a plurality of spaced apart fold lines which permits the integral member to be folded between a mounting position and a protective position or a pair of wing members which are mounted in a scissors arrangement which is movable between a mounting position and a protective position. Upon withdrawing of the needle from the installed position within the body of a human, the wing assembly is automatically positioned to encase the sharpened point of the needle, thereby preventing undesired injury by the needle to the medical practitioner that is installing and removing of the enclosure.

While the devices of the aforementioned patents appear suitable for their intended purposes, the still leave much to be desired from various standpoints, such as simplicity of construction, intuitiveness of operation and ease of use.

SUMMARY OF THE INVENTION

A safety angled indwelling needle device and a protective shield for a safety angled indwelling needle. The safety device comprises the combination of an angled indwelling, e.g., Huber type, needle and a protective shield. The protective shield can be a separate unit for use with an angled Huber needle.

The needle is a hollow member having a distal end portion and a proximal end portion, with the distal end portion extending at an angle to the proximal end portion and terminates in a piercing tip.

The protective shield comprises a central hub and a pair of wing members, e.g., an integrally molded unit. The central hub has a longitudinal central axis, a distal end, a proximal end and a passageway extending through the central hub along the horizontal axis. The proximal end portion of the needle extends through said passageway, e.g., is connected to a tube thereat. The distal end portion of the needle extends out of the passageway in the central hub and extends at an angle, e.g., approximately perpendicularly, to the passageway.

Each of the wing members of the protective shield are generally planar. Each wing member is mounted to the central hub, e.g., secured by a living hinge, on opposite sides of the central hub and is arranged to be moved, e.g., flexed, from an open state, wherein the wing members are generally coplanar with each other, to a closed state, wherein the wing members abut each other with the distal portion of the needle disposed between them, to enclose the needle's piercing tip. Each of the wing members also includes at least one connector, e.g., respective projections and apertures, for holding the wing members in the closed state.

In accordance with one exemplary, but not exclusive embodiment, of this invention each wing member includes include a linear channel therein. The channels conjoin when the wing members are in their closed state to form an enclosed recess for receipt of the needle's piercing tip. Each channel is generally linear and extends within its associated wing member from a first end point adjacent the central hub to a second end point more remote from the hub. The use of the linear channels while not mandatory, desirable, to further ensure that persons contacting the device will not be pierced by the enclosed needle.

In accordance with the aforementioned exemplary embodiment, one of the channels of one of the wing members includes an arrowhead-shaped recess located at the second end point of that wing member. The other of the channels includes an arrowhead shaped projection located at the second end point of the other of the wing member. The arrowhead shaped recess and the arrowhead shaped projection point away from the central hub to provide a visual indication of the direction that the wing members should be flexed when they are in the open state to move them to the closed state. When the wing members are in the closed state the arrowhead shaped projection mates with the arrowhead shaped recess so as not to interfere with the formation of the enclosed recess for the piercing tip when the two wing members are in their closed state.

DETAILED DESCRIPTION OF THE PREFERRED EMBODIMENT

Figure 1:
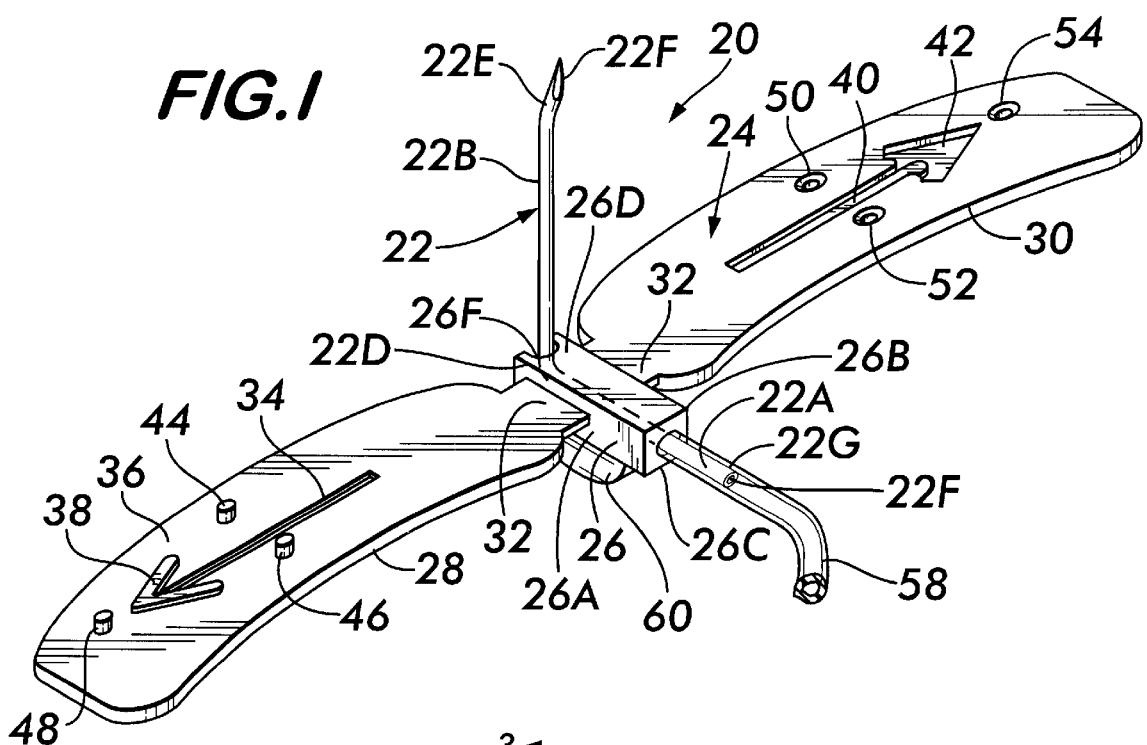
FIG. 1 is an isometric view of one embodiment of a safety angled indwelling needle device with its protective shield in the open condition ready for use.

Referring to FIG. 1, there is shown at 20 one exemplary embodiment of a safety indwelling needle device constructed in accordance with this invention. It should be pointed out at this juncture that the device 20 shown in FIG. 1 comprises the preassembled combination a conventional angled indwelling, e.g., Hubertype, needle 22 and a protective shield 24 for the needle. The subject invention also contemplates use of a separate shield 24 for selective mounting on any conventional angled indwelling needle to result in an assembly constructed similarly to the device 20.

Figure 3:
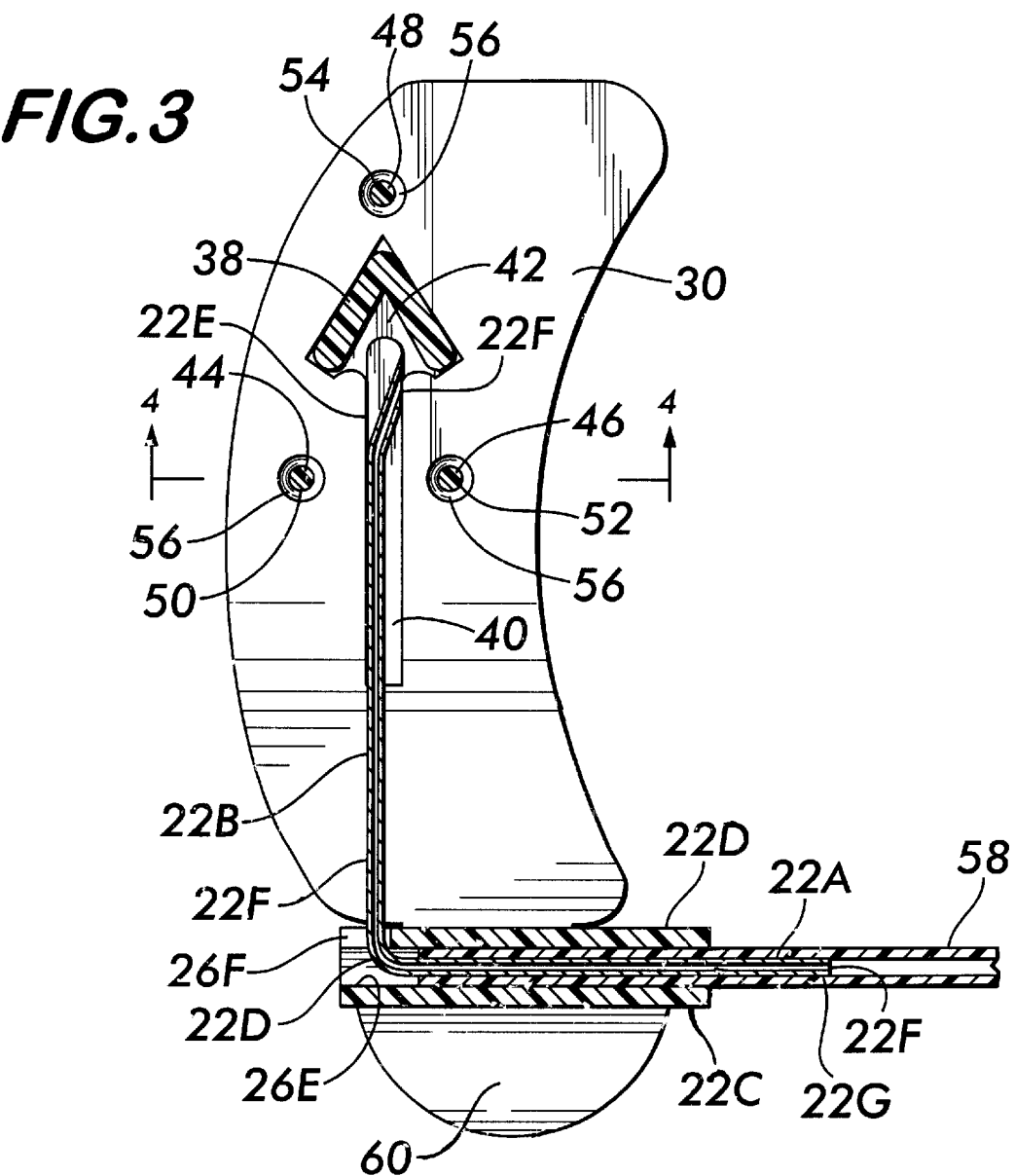
FIG. 3 is a sectional view taken along line 3—3 of FIG. 2.
Figure 4:
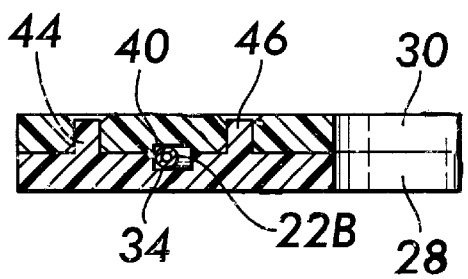
FIG. 4 is an enlarged sectional view taken along line 4—4 of FIG. 3.

The exemplary needle 22 is a conventional Hubertype device. Thus, all the details of its construction will not be reiterated herein in the interests of brevity. Suffice it to state that the needle 22 is a hollow tubular member, e.g., a stainless steel tube, having a linear proximal end portion 22A and a linear distal end portion 22B terminating in an angularly extending free end 22C. The distal end portion 22A extends generally perpendicularly to the proximal end portion 22B at point 22D. The free end 22C is also somewhat linear, but extends at an acute angle to the axis of the distal end portion 22B and includes a sharpened tip 22E in the form of a beveled end free end (FIGS. 1 and 3). The needle 22 includes a central passageway 22F (FIGS. 1 and 3) extending its entire length from the open beveled free end or tip 22E to the proximal end 22G of the proximal end portion 22B.

It should be pointed out at this juncture that the needle 22 is merely exemplary of various types of angled, indwelling needles that can be used with the subject invention. Thus, the needle need not be a Huber type, e.g., one whose distal end is offset or angled, but can be one whose distal end portion is linear or curved or a combination thereof.

The shield basically comprises an integral unit, e.g., a molded biocompatible plastic member, having central hub 26 from which a pair of generally planar wings 28 and 30 project outward. In particular, the hub 26 is an elongated member of generally rectangular cross section having a pair of sidewalls 26A and 26B, a top wall 26C and a bottom wall 26D. The wing 28 projects outward from the sidewall 26A and is a planar member which normally lies in a plane parallel to the top and bottom walls, 26C and 26D, respectively of the hub 28. In a similar manner the wing 30 projects outward from the sidewall 26B and is a planar member which normally lies in a plane parallel to the top and bottom walls, 26C and 26D, respectively of the hub 26.

The needle 22 is fixedly secured with respect to the shield 24. To that end the hub 26 includes a central passageway 26E extending therethrough. The proximal end portion 22A of the needle 22 is located and held within that passageway, as will be described later. A notch 26F is located at the end of the hub in the bottom wall 26D to receive and hold the right angle oriented distal end portion 22B of the needle 22 so that it is perpendicular to the plane of the wings 28 and 30 when those wings are in their opened, coplanar orientation shown in FIG. 1.

Figure 2:
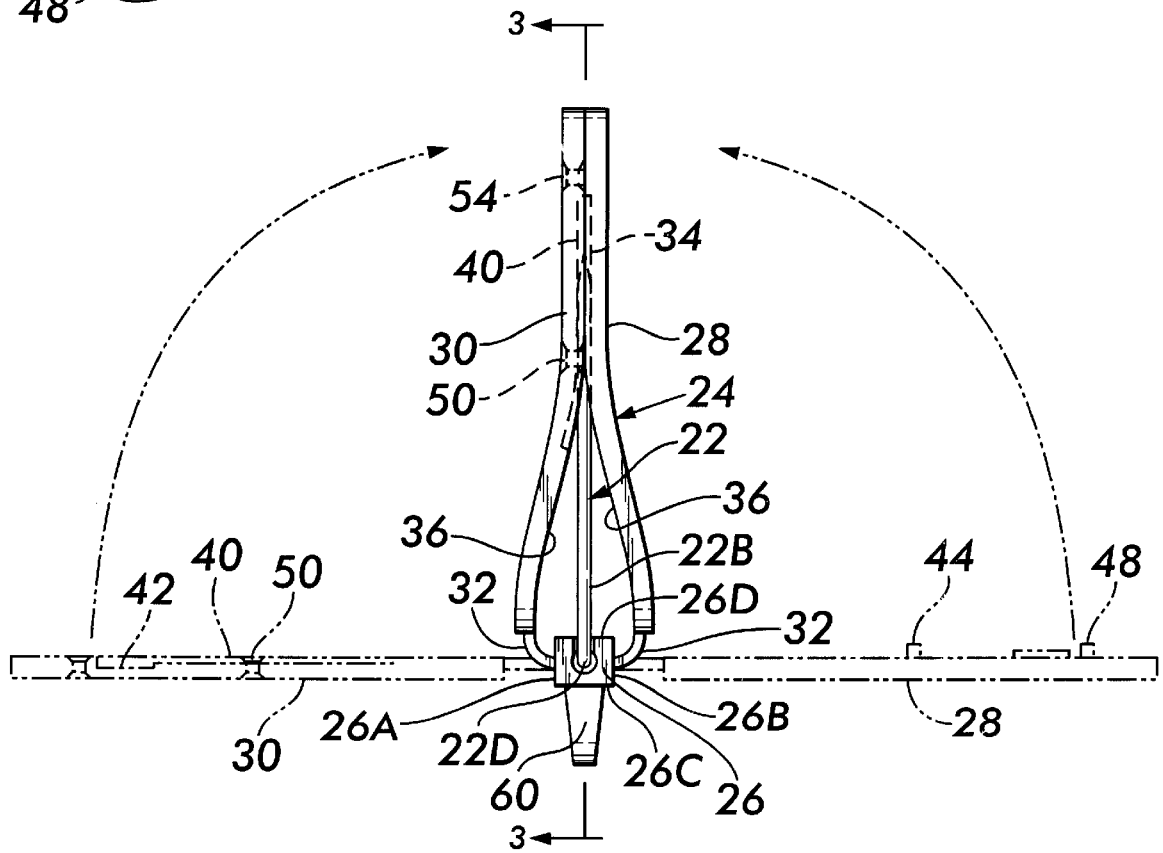
FIG. 2 is an end view of the device of FIG. 1 showing the protective shield in its closed condition to protect persons from coming into contact with the sharp tip of the needle, and showing by means of phantom lines the shield in the open condition of FIG. 1.

The wings 28 and 30 are arranged to be flexed or pivoted from their open and coplanar orientation shown in FIG. 1 and by the phantom lines in FIG. 2, to the closed orientation shown in FIG. 2. The direction of flexure of the wings is shown by the phantom line arrows in FIG. 2.

In the closed position, the wings abut each other at their distal end portions in a plane generally perpendicular to the plane in which they were disposed in their open orientation, and with the distal end portion 22B of the needle 22 disposed therebetween to protect users of the device 20 from an accidental needle-stick.

In order to facilitate the flexing or pivoting of the wings from their open position to their closed position the portions 32 of the wings 28 and 30 contiguous with the hub 26 are of a reduced width and thickness to create a living hinge. Moreover, the plastic forming the wings is preferably somewhat flexible, thereby enabling the wings to flex or bend readily at their hinges 32.

As best seen in FIGS. 1–3 each wing includes a recess or slot therein which are arranged to conjoin to form a channel in which the distal end portion 22B of the needle is located when the device 20 is in its closed state. In particular, the wing 28 includes a slot 34 extending down the a portion of the inner surface 36 of the wing 28 aligned with the point 22D at which the distal end portion 22B projects perpendicularly to the proximal end portion 22A of the needle 22. The slot 34 extends from approximately the middle of the length of the wing to a point adjacent the wings free end. The distal end of the slot 34 terminates in an upstanding generally arrowhead shaped wall 38 projecting slightly upward from the inner surface 36 of the wing 28. The function of the projection or wall 38 will be described later. In a similar manner the wing 30 includes a slot 40 extending down the a portion of the inner surface 36 of the wing 30 aligned with the point 22D at which the distal end portion 22B projects perpendicularly to the proximal end portion 22A of the needle 22. The slot 40 also ends from approximately the middle of the length of the wing to a point adjacent the wings free end. The distal end of the slot 40 terminates in a generally arrowhead shaped recess 42. The function of the arrowhead shaped recess 42 will also be described later.

As can be seen in FIG. 2 when the two wings 28 and 30 are flexed to their closed orientation their slots 34 and 40 respectively form an enclosed channel in which the sharpened free end 22F and contiguous portion of the distal end portion 22B of the needle is located and confined. This action effectively prevents anyone in contact with the device 20 from accidentally receiving a needle-stick from the needle. In order to hold the wings in their closed orientation against the natural bias of the material forming the wings which tends to try and return them to their opened orientation, the device 20 includes plural releasably securable connectors. In particular, in the case of the illustrated exemplary embodiment, wing 28 includes a plurality, e.g., three, short cylindrical posts 44,46 and 48 projecting upward from the inner surface 36 of the wing 28. The posts 44 and 46 are aligned on opposite sides of the slot 34 at approximately the middle of the slot. The post 48 is located adjacent the apex of the arrowhead shaped projecting wall 38 and is axially aligned with the slot 34. The wing 30 includes a plurality, e.g., three, circular holes or apertures 50, 52 and 54 extending inward into the wing from the inner surface 36 of the wing. The inside diameter of each of the apertures 50, 52 and 54 is just slightly less than the outside diameter of the posts 44, 46, and 48, respectively, to releasably receive the posts therein and to hold them in place therein against accidental disconnection. To that end the holes 50 and 52 are aligned on opposite sides of the slot 40 at approximately the middle of the slot so that the are axially aligned with the posts 44 and 46 when the wings are in their closed orientation. The post 54 is located adjacent the apex of the arrowhead shaped recess 42 and is axially aligned with the slot 40. The hole 54 is also axially aligned with the posts 48 when the wings are in their closed orientation. In order to facilitate the entry of the posts 44, 46 and 48 into the holes 50, 52 and 54, respectively, each of the holes includes a flared entryway or mouth 56 (FIG. 3).

As best seen in FIGS. 1 and 3 a length conventional flexible tubing 58 is mounted on the proximal end portion 22A of the needle 22. This tubing is arranged to carry the liquid which is to be introduced by the needle. The inside diameter of the passageway 26E of the hub 26 is approximately the same as the outside diameter of the tubing 58 to 4E receive it and hold it in place, thereby holding the proximal end portion 22A of the needle within that passageway. The notch 26F serves to prevent the needle from twisting about the longitudinal axis of the passageway, thereby holding the distal end portion of the needle perpendicular to the plane of the wings when the wings are in their opened orientation. Thus, the device can be applied to the user by securing the wings to the skin of the user at the situs of the needle entry point, whereupon the distally located portion of the needle will project through the skin of the patient, e.g., into the implanted port.

As best seen in FIGS. 1 and 3 a short flange 60 is provided upstanding from the top wall 26C of the central hub 26 to serve as a portion that can be grasped between the user's fingers to hold the device 20 and facilitate its mounting and dismounting with respect to the patient.

Without further elaboration the foregoing will so fully illustrate my invention that others may, by applying current or future knowledge, adopt the same for use under various conditions of service.

I claim:

1. A safety Huber angled needle device, said device comprising a Huber needle and a protective shield, said Huber needle comprising a hollow member having a distal end portion and a proximal end portion, said distal end portion extending at an angle to said proximal end portion and terminating in a piercing tip, said protective shield comprising a central hub and a pair of first and second wing members, said central hub having diametrically opposed sides, a longitudinal central axis, a distal end, a proximal end and a passageway extending through said central hub along said longitudinal central axis, said proximal end portion of said Huber needle extending through said passageway so that said distal end portion of said Huber needle extends out of said passageway and at an angle to said longitudinal central axis, said first and second wing members each being a generally planar member having an inner surface, a free end and a fixed end, said fixed end of said first wing member being connected to said central hub at one of said sides, said fixed end of said second wing member being connected to said central hub at the other of said sides, whereupon said first and second wing members are connected to said central hub diametrically opposed from each other, each of said first and second wing members being arranged to be moved from an open state, wherein said first and second wing members are generally coplanar with each other, to a closed state, wherein said inner surfaces of said first and second wing members contiguous with their free ends abut each other with said distal portion of said Huber needle disposed between said inner surfaces of said first and second wing members to enclose said piercing tip, said inner surface of each of said first and second wing members including at least one connector, said at least one connector of said first wing member being arranged for engagement with said at least one connector of said second wing member for holding said first and second wing members in said closed state.

2. The device of claim 1 wherein at least one of said wing members includes a channel therein for receipt of said piercing tip when said wing members are in said closed state.

3. The device of claim 2 wherein both of said wing members include a channel therein, said channels conjoining when said wing members are in said closed state to form an enclosed recess for receipt of said piercing tip.

4. The device of claim 3 wherein each channel is generally linear and extends within its associated wing member from a first end point adjacent said central hub to a second end point more remote from said central hub, and wherein one of said channels of one of said wing members includes an arrowhead-shaped recess located at said second end point of said one of said wing members and wherein the other of said channels includes an arrowhead shaped projection located at said second end point of the other of said wing members, said arrowhead shaped projection being arranged to fit within said arrowhead shaped recess when said wing members are in said closed state.

5. The device of claim 1 wherein said at least one connector comprise at least one projection and at least one cooperating bore.

6. The device of claim 5 wherein one of said wing portions includes said at least one projection and wherein the other of said wing members includes said at least one bore.

7. The device of claim 6 wherein said at least one projection comprises post and wherein said at least one bore comprises an aperture whose cross sectional area is approximately equal to that of said post to tightly receive said post therein.

8. The device of claim 7 wherein said aperture includes a flared mouth for facilitating entry of said post into said aperture.

9. The device of claim 8 wherein said device comprises plural apertures and plural cooperating posts.

10. The device of claim 1 wherein said wing members are flexible to bend from said open state to said closed state.

11. The device of claim 1 wherein said shield is formed of a moldable material and wherein said wing members are connected to said central hub on opposite sides thereof by respective living hinges.

12. The device of claim 11 wherein said wings are flexible.

13. The device of claim 1 additionally comprising a flange upstanding from said central hub, said flange extending in the opposite directions than said wing members when said wing members are in said closed state.

14. The device of claim 13 wherein said central hub is of a generally rectangular cross sectional area.

15. The device of claim 1 additionally comprising a tube connected to said proximal end portion of said Huber needle.

16. A protective shield for a Huber angled needle, said Huber needle comprising a hollow member having a distal end portion and a proximal end portion, the distal end portion extending at an angle to the proximal end portion and terminating in a piercing tip, said protective shield comprising a central hub and a pair of wing members, said central hub having diametrically opposed sides, a longitudinal central axis, a distal end, a proximal end and a passageway extending through said central hub along said longitudinal central axis, said passageway being adapted to receive the proximal end portion of the Huber needle extending through it so that the distal end portion of the Huber needle extends out of said passageway and at an angle to said longitudinal central axis, each of said wing members being a generally planar member having an inner surface, a free end and a fixed end, said fixed end of said first wing member being connected to said central hub at one of said sides, said fixed end of said second wing member being connected to said central hub at the other of said sides, whereupon said first and second wing members are connected to said central hub diametrically opposed from each other, each of said first and second wing members being arranged to be moved from an open state, wherein said first and second wing members are generally coplanar with each other, to a closed state, wherein said inner surfaces of said first and second wing members abut each other with the distal portion of the Huber needle disposed between said inner surfaces of said first and second wing members to enclose the piercing tip of the Huber needle, said inner surface of each of said first and second wing members including at least one connector, said at least one connector of said first wing member being arranged for engagement with said at least one connector of said second wing member for holding said first and second wing members in said closed state.

17. The shield of claim 16 wherein at least one of said wing members includes a channel therein for receipt of the piercing tip of the Huber needle when said wing members are in said closed state.

18. The shield of claim 17 wherein both of said wing members include a channel therein, said channels conjoining when said wing members are in said closed state to form an enclosed recess for receipt of the piercing tip of the Huber needle.

19. The shield of claim 16 wherein said at least one connector comprise at least one projection and at least one cooperating bore.

20. The shield of claim 19 wherein one of said wing portions includes said at least one projection and wherein the other of said wing members includes said at least one bore.

21. The shield of claim 16 wherein said wing members are flexible to bend from said open state to said closed state.

22. The shield of claim 16 wherein said shield is formed of a moldable material and wherein said wing members are connected to said central hub on opposite sides thereof by respective living hinges.

23. The shield of claim 12 wherein said wings are flexible.

\* \* \* \* \*